US012576056B2

(12) United States Patent     (10) Patent No.:   US 12,576,056 B2
Nagai et al.          (45) Date of Patent:     Mar. 17, 2026

(54) AMINO ACID-CONTAINING GRANULES

(71) Applicant: MEIJI CO., LTD., Tokyo (JP)

(72) Inventors: Takuya Nagai, Tokyo (JP); Akio Tanaka, Tokyo (JP)

(73) Assignee: MEIJI CO., LTD., Tokyo (JP)

( * ) Notice: Subject to any disclaimer, the term of this patent is extended or adjusted under 35 U.S.C. 154(b) by 953 days.

(21) Appl. No.: 17/761,760

(22) PCT Filed: Sep. 18, 2020

(86) PCT No.: PCT/JP2020/035526
§ 371 (c)(1),
(2) Date: Mar. 18, 2022

(87) PCT Pub. No.: WO2021/054453
PCT Pub. Date: Mar. 25, 2021

(65) Prior Publication Data
US 2022/0378733 A1     Dec. 1, 2022

(30) Foreign Application Priority Data
Sep. 20, 2019   (JP) ................................ 2019-172259

(51) Int. Cl.
*A61K 31/198*     (2006.01)
*A61K 9/16*       (2006.01)

(52) U.S. Cl.
CPC .............. *A61K 31/198* (2013.01); *A61K 9/16* (2013.01)

(58) Field of Classification Search
CPC ...... A61K 31/198; A61K 9/16; A61K 9/0053; A23L 33/175
See application file for complete search history.

(56) References Cited

U.S. PATENT DOCUMENTS

| | | | |
|---|---|---|---|
| 2010/0178350 A1 | 7/2010 | Ida et al. | |
| 2015/0104517 A1* | 4/2015 | Ida ........................ | A23L 33/175 |
| | | | 514/561 |
| 2019/0045825 A1 | 2/2019 | Mukouyama et al. | |

FOREIGN PATENT DOCUMENTS

| | | | | |
|---|---|---|---|---|
| CN | 1731990 | 2/2006 | | |
| CN | 101765426 | 6/2010 | | |
| JP | 2002-145769 | 5/2002 | | |
| JP | 2004-210639 | 7/2004 | | |
| JP | 2008-162955 | 7/2008 | | |
| JP | 2008-239586 | 10/2008 | | |
| JP | 2012-36140 | 2/2012 | | |
| JP | 2014-205661 | 10/2014 | | |
| WO | 02/38147 | 5/2002 | | |
| WO | WO-0238147 A1 * | 5/2002 | .......... | A61K 31/195 |
| WO | 2017/183628 | 10/2017 | | |

OTHER PUBLICATIONS

International Search Report issued Dec. 1, 2020 in connection with International (PCT) Application No. PCT/JP2020/035526.
Office Action issued Jun. 13, 2024 in Chinese Patent Application No. 202080065685.1, with English-language Translation.
Office Action issued Jul. 9, 2024 in Japanese Patent Application No. 2021-546988, with English-language Translation.
Office Action issued Jan. 17, 2024 in corresponding Chinese Patent Application No. 202080065685.1, with English translation.
Office Action issued Dec. 10, 2024 in Japanese Patent Application No. 2021-546988, with English-language Translation.
Chinese Office Action issued Jul. 5, 2023 in corresponding Chinese Patent Application No. 202080065685.1, with English translation.

* cited by examiner

*Primary Examiner* — Susan T Tran
*Assistant Examiner* — William Craigo
(74) *Attorney, Agent, or Firm* — Wenderoth, Lind & Ponack, L.L.P.

(57)       ABSTRACT
An embodiment of the present invention relates to amino acid-containing granules containing an amino acid as a main component, the amino acid-containing granules having an average particle diameter of 150 μm to 500 μm and a homogeneity U of 0.70 or less, in which the average particle diameter and the homogeneity U are determined by the following measurement method.

13 Claims, 2 Drawing Sheets

FIG. 2

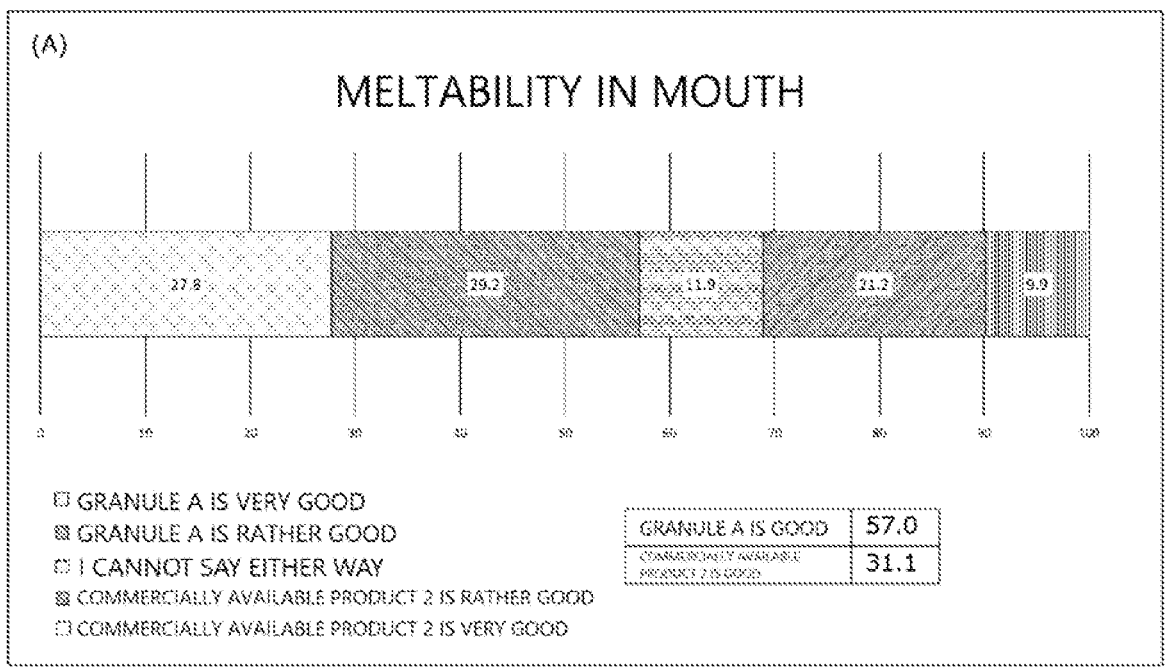

(A)

MELTABILITY IN MOUTH

□ GRANULE A IS VERY GOOD
▨ GRANULE A IS RATHER GOOD
▢ I CANNOT SAY EITHER WAY
▨ COMMERCIALLY AVAILABLE PRODUCT 2 IS RATHER GOOD
□ COMMERCIALLY AVAILABLE PRODUCT 2 IS VERY GOOD

| GRANULE A IS GOOD | 57.0 |
|---|---|
| COMMERCIALLY AVAILABLE PRODUCT 2 IS GOOD | 31.1 |

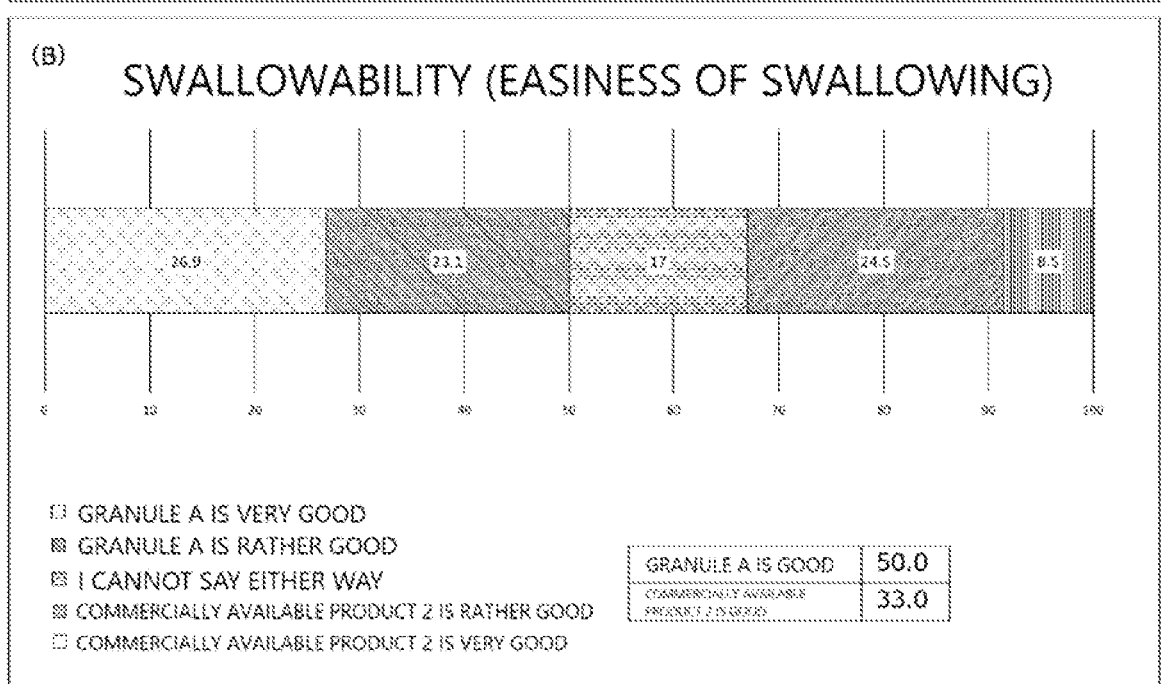

(B)

SWALLOWABILITY (EASINESS OF SWALLOWING)

□ GRANULE A IS VERY GOOD
▨ GRANULE A IS RATHER GOOD
▨ I CANNOT SAY EITHER WAY
▨ COMMERCIALLY AVAILABLE PRODUCT 2 IS RATHER GOOD
□ COMMERCIALLY AVAILABLE PRODUCT 2 IS VERY GOOD

| GRANULE A IS GOOD | 50.0 |
|---|---|
| COMMERCIALLY AVAILABLE PRODUCT 2 IS GOOD | 33.0 |

AMINO ACID-CONTAINING GRANULES

TECHNICAL FIELD

The present invention relates to amino acid-containing granules containing an amino acid as a main component.

BACKGROUND ART

An amino acid is known to have various effects such as muscle building, fatigue recovery, body fat reduction, and immunity improvement. For example, arginine, which is one of basic amino acids, has various physiologically activity such as promoting secretion of a growth hormone and improving basal metabolism, and is one of useful amino acids. Therefore, various amino acid-containing granules have been developed as a supplement for supplying an amino acid.

Patent Literature 1 describes amino acid-containing granules and a method for producing the same. The production method includes a step of adding 10 to 17 parts by weight of ethanol to 100 parts by weight of a raw material for granulation containing amino acid particles having a volume-based median diameter of 60 μm to 90 μm, and a step of granulating the mixture.

CITATION LIST

Patent Literature

Patent Literature 1: JP-A-2014-205661

SUMMARY OF INVENTION

Technical Problem

The amino acid-containing granules may be taken directly orally without being dissolved in water or the like, or taken orally after being dissolved in water or the like. However, when an amino acid is blended at a high concentration by using the common production method described above, it is difficult to stably granulate granules that can melt easily in the mouth when taken directly orally. For this reason, the amino acid-containing granules do not melt very well and is difficult to be swallowed.

In addition, such amino acid-containing granules have poor settleability in water when dissolved in water, and it is difficult to improve the solubility in water. For this reason, a large amount of undissolved amino acid remain, and this makes it difficult to swallow the mixture.

Therefore, an object of the present invention is to provide amino acid-containing granules that can melt easily in the mouth and are excellent in swallowability (easiness of swallowing) when taken directly orally. Another object of the present invention is to provide amino acid-containing granules that can be sufficiently dissolved in water and are capable of preparing an amino acid solution having less undissolved amino acid and being easily swallowed.

Solution to Problem

As a result of intensive studies, the present inventors have found that the above problems can be solved by setting an average particle diameter and a homogeneity U defined below within specific ranges in amino acid-containing granules containing an amino acid as a main component, and have completed the present invention.

That is, the present invention is as follows.

[1] Amino acid-containing granules containing an amino acid as a main component, wherein the amino acid-containing granules have an average particle diameter of 150 μm to 500 μm, and a homogeneity U of 0.70 or less, and wherein the average particle diameter and the homogeneity U are determined by the following measurement method:

[Average Particle Diameter and Homogeneity U]

1. a volume-based particle size distribution in which data is plotted with the particle diameter as a horizontal axis and with the content ratio of particles as a vertical axis is obtained for the granules by a laser diffraction and scattering measurement method,
2. the average particle diameter is determined from the volume-based particle size distribution, and
3. the homogeneity U is determined by the following formula (1).

[Formula 1]

$$U = \frac{\sum X_i |D_i - D_p|}{D_p} \tag{1}$$

In the formula (1), $D_p$ is an average particle diameter (μm), $X_i$ is a content ratio of particles at each particle diameter in the volume-based particle size distribution, and $D_i$ is a particle diameter (μm) of each particle.

[2] The amino acid-containing granules according to [1], wherein the amino acid-containing granules have a specific surface area of 0.30 m²/g or more.

[3] The amino acid-containing granules according to [1] or [2], wherein the amino acid-containing granules have a content ratio (volume ratio) of a fine powder having a particle diameter of 100 μm or less of 25% or less.

[4] The amino acid-containing granules according to any one of [1] to [3], wherein the amino acid-containing granules have a bulk specific gravity of 0.3 g/mL or more.

[5] The amino acid-containing granules according to any one of [1] to [4], wherein the amino acid-containing granules have an amino acid content of 50 mass % or more.

[6] The amino acid-containing granules according to any one of [1] to [5], wherein the amino acid-containing granules have a powdering ratio of 5% or more, and in which the powdering ratio means a value obtained by the following procedure (1) to (5), (1) the amino acid-containing granules are sieved with a sieve having a size of mesh opening of 250 μm for 1 minute at a frequency of 100 times/sec and an amplitude of 2 mm, and granules having a particle diameter of 250 μm or less are removed, (2) 10 g of granules remaining on the sieve is weighed out and taken as a "weight of original sample granules", (3) 10 g of the granules weighed in (2) above is put into the sieve having a size of mesh opening of 250 μm with five tapping halls (diameter: 20 mm), and wear and impact are applied to the granules at a frequency of 100 times/sec and an amplitude of 2 mm for 15 minutes, (4) a weight of granules dropped under the sieve is measured, and is defined as a "weight of newly generated fine powder", and (5) the powdering ratio is determined by the following formula.

Powdering ratio (%)=(weight of newly generated fine powder/weight of original sample granules)×100

[7] The amino acid-containing granules according to any one of [1] to [6], in which a residual weight of the granules is 1 g or less, when 7 g of the granules is added to 100 ml of water and stirred, then the mixture is sieved with a sieve having a size of mesh opening of 150 μm, and granules remaining on the sieve are dried at 98° C. for 4 hours.

[8] The amino acid-containing granules according to any one of [1] to [7], further including at least one selected from the group consisting of a carbohydrate, an acidulant, a fragrance, a sweetener, and a thickening polysaccharide.

[9] A method for producing the amino acid-containing granules according to any one of [1] to [8], including: a mixing step of mixing an amino acid powder and other components; and a granulation step of granulating the mixture obtained in the mixing step.

[10] The production method according to [9], further including: a step of classifying the granules obtained in the granulation step by sieving.

Advantageous Effects of Invention

The present invention allows for providing amino acid-containing granules that can melt easily in the mouth and are excellent in swallowability (easiness of swallowing) when taken directly orally, as the average particle diameter and the homogeneity U are within the specific ranges.

In addition, the present invention allows for providing amino acid-containing granules that can be sufficiently dissolved in water. When the granules are sufficiently dissolved in water, it is possible to prepare an amino acid solution having less undissolved amino acid and being easily swallowed when the granules are taken orally after being dissolved in water.

BRIEF DESCRIPTION OF DRAWINGS

FIG. 2 provides diagrams illustrating results of a sensory test of granule A produced in Examples and a commercially available product 2. (A) of FIG. 2 shows an evaluation result of a meltability in the mouth, and (B) of FIG. 2 shows an evaluation result of swallowability (easiness of swallowing).

DESCRIPTION OF EMBODIMENTS

Figure 1:
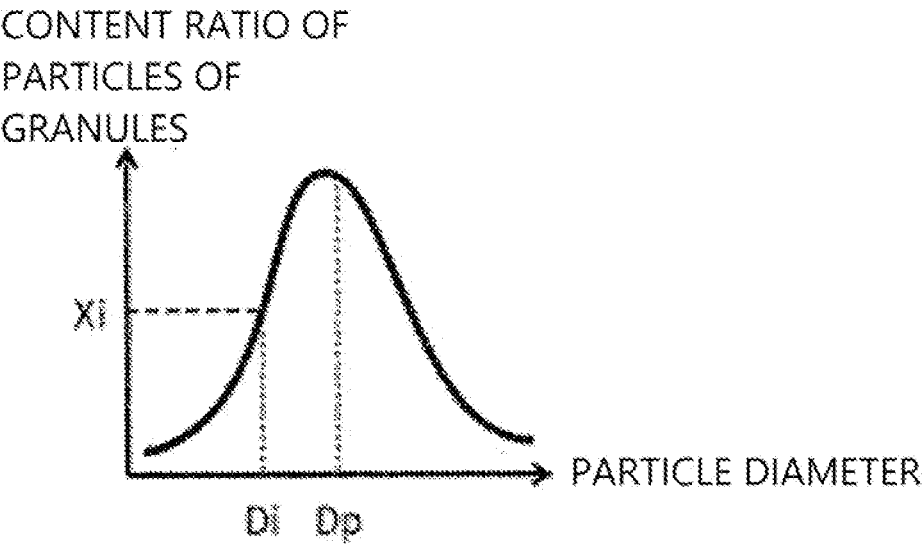
FIG. 1 is a graph for illustrating a homogeneity U.

Hereinafter, an embodiment of the present invention will be described in more detail.

An embodiment of the present invention is amino acid-containing granules containing an amino acid as a main component and having an average particle diameter and a homogeneity U within specific ranges.

In the amino acid-containing granules of the present embodiment (hereinafter, may be simply referred to as granule), the average particle diameter and the homogeneity U are set to specific ranges. This allows for providing the amino acid-containing granules that can melt easily in the mouth and are excellent in swallowability (easiness of swallowing) when taken directly orally.

In addition, amino acid-containing granules that can be sufficiently dissolved in water can be provided. When the granules are sufficiently dissolved in water, it is possible to prepare an amino acid solution having less undissolved amino acid and being easily swallowed when the granules are taken orally after being dissolved in water.

In the present embodiment, it is presumed that the reason why a good meltability in the mouth and sufficiently high water solubility is imparted by adjusting the average particle diameter and the homogeneity U to specific ranges is as follows. That is, granules having a large particle diameter have a small specific surface area and a small contact area with water or the like, and thus it takes time to dissolve the granules. Granules having a small particle diameter are easy to scatter, leads to choking and sticking to a throat, and thus the granules are hard to be swallowed. Granules having a small particle diameter have a large specific surface area, form a lump in which only a surface of the granules is wet, and this results in a decrease in solubility. In the present embodiment, the solubility is improved and the easiness of swallowing is improved by specifying the ranges of the average particle diameter and the homogeneity U. It should be noted that the present embodiment is not limited to the one that exhibits the above-described effects.

The amino acid contained in the amino acid-containing granules according to the present embodiment is not limited, but examples of the amino acid include arginine, lysine, ornithine, phenylalanine, tyrosine, valine, methionine, leucine, isoleucine, tryptophan, histidine, proline, cysteine, glutamic acid, asparagine, aspartic acid, serine, glutamine, citrulline, creatine, methyllysine, acetyllysine, hydroxylysine, hydroxyproline, glycine, alanine, threonine, and cystine. These may be used alone or in combination.

The amino acid contained in the amino acid-containing granules according to the present embodiment may be either a natural product or a synthetic product, and a simple amino acid or a mixture of two or more kinds of amino acids can be used. As the amino acid, not only free amino acids but also salts such as sodium salt, hydrochloride, and acetate and derivatives such as carnitine and ornithine can be used.

As used herein, the term "amino acid" includes α-amino acid, β-amino acid, and γ-amino acid. The amino acid may be either L-optical or D-optical.

The amino acid-containing granules according to the present embodiment contain an amino acid as a main component. Here, the "main component" means a component having the highest content ratio (on a mass basis) among all components of the granules.

A content of the amino acid in the granules is preferably 30 mass % or more, more preferably 35 mass % or more, still more preferably 40 mass % or more, still further more preferably 45 mass % or more, yet still more preferably 50 mass % or more, yet still further more preferably 55 mass % or more, even more preferably 60 mass % or more, still even more preferably 65 mass % or more, and yet still even more preferably 70 mass % or more, with respect to the granules.

When the content of the amino acid in the granules is within the above range, the granules have high purity of the amino acid. The amino acid-containing granules according to the present embodiment have a specific average particle diameter and homogeneity, and thus, the granules can melt easily in the mouth and can be sufficiently dissolved in water, even if the granules have such a high concentration of amino acid.

An upper limit of the content of the amino acid in the amino acid-containing granules according to the present embodiment is not limited, but is, for example, 99 mass % or less, 95 mass % or less, or 90 mass % or less, with respect to the granules.

The amino acid-containing granules according to the present embodiment have an average particle diameter of 150 μm to 500 μm. When the average particle diameter is within the above range, the amino acid-containing granules that can melt easily in the mouth and have good swallowability (easiness of swallowing) when taken directly orally can be obtained. In addition, when the average particle diameter is within the above range, the solubility of the granules in water sufficiently increases, and this allows for preparing an amino acid solution that has less undissolved amino acid and is easily swallowed.

The average particle diameter of the amino acid-containing granules according to the present embodiment is preferably 160 µm or more, more preferably 170 µm or more, still more preferably 180 µm or more, yet still more preferably 190 µm or more, still further more preferably 200 µm or more, and yet still further more preferably 210 µm or more. The average particle diameter of the amino acid-containing granules according to the present embodiment may be 450 µm or less or 400 µm or less.

The average particle diameter of the amino acid-containing granules according to the present embodiment can be determined from a volume-based particle size distribution obtained by a laser diffraction and scattering measurement method in which data is plotted with a particle diameter as a horizontal axis and with a content ratio of particles as a vertical axis, as shown in FIG. 1. Specifically, the average particle diameter can be determined from the volume-based particle size distribution based on the following formula.

$$D_p = \frac{\sum_{i=1}^{n} X_i * D_i^4}{\sum_{i=1}^{n} X_i * D_i^3}$$ [Formula 2]

In the above formula, $D_p$ is an average particle diameter (µm), $D_i$ is any particle diameter (µm), and $X_i$ is a content ratio (volume ratio) of particles of the granules at $D_i$. Here, the content ratio (volume ratio) of particles of the granules at $D_i$ means a ratio of a volume of the granules having the particle diameter $D_i$ to a volume of the entire granules, and means $V_i/V$ where V is the volume of the entire granules, and $V_i$ is the volume of the granules having the particle diameter D.

In the present embodiment, a median diameter of a volume-based frequency distribution can be measured using a laser diffraction and scattering particle size distribution measuring device, and the median diameter can be defined as an average particle diameter. As the laser diffraction and scattering particle size distribution measuring device, for example, Mastersizer 3000 (trade name) manufactured by Malvern Co., Ltd. and the included soft Mastersizer 3000 can be used.

The amino acid-containing granules according to the present embodiment need to have a homogeneity U of 0.70 or less. The homogeneity U refers to a value represented by the following formula (1), and when the value is low, granules in which the particle size distribution of the granules is sharp is obtained. When the homogeneity U is in the above range, the amino acid-containing granules can melt easily in the mouth, and can be sufficiently dissolved in water.

The homogeneity U of the amino acid-containing granules is preferably 0.68 or less, and more preferably 0.65 or less. A lower limit of the homogeneity U of the amino acid-containing granules is, for example, 0.35 or more, 0.40 or more, or 0.45 or more.

The homogeneity U of the amino acid-containing granules according to the present embodiment can be measured using the Mastersizer 3000 (trade name) manufactured by Malvern Co., Ltd. and the included soft Mastersizer 3000 as the laser diffraction and scattering particle size distribution measuring device, in the similar manner to the measurement of the average particle diameter described above.

Hereinafter, the homogeneity U will be described with reference to FIG. 1. In FIG. 1, when $D_p$ is defined as an average particle diameter (µm), which is a median diameter of a volume-based frequency distribution, and $D_i$ is defined as an particle diameter (µm) of any particles of the granules, a content ratio (volume ratio) of the particles of the granules at $D_i$ is represented by $X_i$. The particle size distribution of the particles of the granules, that is, the homogeneity U can be expressed by the following formula (1). A numerator of formula (1) is a sum of values obtained by multiplying a difference between the particle diameter $D_i$ and the average particle diameter $D_p$ of any particles by the content ratio $X_i$, and the homogeneity U is a value obtained by dividing the sum by the average particle diameter D.

In formula (1), the symbol "‖" represents an absolute value. The content ratio (volume ratio) of the particles of the granules in $D_i$ means a ratio of the volume of the granules having the particle diameter $D_i$ to the volume of the entire granules, and means $V_i/V$ where V is the volume of the entire granules, and $V_i$ is the volume of the granules having the particle diameter $D_i$.

[Formula 3]

$$U = \frac{\sum X_i |D_i - D_p|}{D_p}$$ (1)

As can be seen from the above formula (1), the sharper particle size distribution of the particles of the granules equates to the lower value of the homogeneity U. In the present embodiment, as described above, the homogeneity U needs to be 0.70 or less, and it can be said that the particle size distribution is narrow.

The amino acid-containing granules according to the present embodiment preferably have a content ratio (volume ratio) of a fine powder having a particle diameter of 150 µm or more of 40% or less. When the content ratio of the fine powder having a particle diameter of 150 µm or less is in the above range, the amino acid-containing granules can melt easily in the mouth, and can be sufficiently dissolved in water. When the content ratio of the fine powder having a particle diameter of 150 µm or less is in the above range, the amino acid-containing granules are also less likely to cause choking when taken directly orally.

The content ratio (volume ratio) of the fine powder having a particle diameter of 150 µm or less is preferably 36% or less, and more preferably 32% or less.

The content ratio (volume ratio) of the fine powder having a particle diameter of 150 µm or less is, for example, 4% or more and 6% or more.

The amino acid-containing granules according to the present embodiment preferably have a content ratio (volume ratio) of a fine powder having a particle diameter of 100 µm or less of 25% or less. When the content ratio of the fine powder having a particle diameter of 100 µm or less is in the above range, the amino acid-containing granules can melt easily in the mouth, and can be sufficiently dissolved in water. When the content ratio of the fine powder having a particle diameter of 150 µm or less is in the above range, the amino acid-containing granules are also less likely to cause choking when taken directly orally.

The content ratio (volume ratio) of the fine powder having a particle diameter of 100 µm or less is preferably 23% or less, more preferably 20% or less, and still more preferably 18% or less.

The content ratio (volume ratio) of the particles having a particle diameter of 100 µm or more is, for example, 3% or more or 8% or more.

The amino acid-containing granules according to the present embodiment preferably have a content ratio (volume ratio) of a fine powder having a particle diameter of 50 or less of 12% or less. When the content ratio of the fine powder having a particle diameter of 50 µm or less is in the above range, the amino acid-containing granules can melt easily in the mouth, and can be sufficiently dissolved in water. When the content ratio of the fine powder having a particle diameter of 150 µm or less is in the above range, the amino acid-containing granules are also less likely to cause choking when taken directly orally.

The content ratio (volume ratio) of the fine powder having a particle diameter of 50 µm or less is preferably 7% or less, and more preferably 6% or less.

The content ratio (volume ratio) of the particles having a particle diameter of 50 µm or more is, for example, 0.5% or more and 1% or more.

The content ratio (volume ratio) of the particles having the above particle diameter can be determined from the volume-based particle size distribution obtained by the laser diffraction and scattering measurement method in which data is plotted with the particle diameter as a horizontal axis and with the content ratio of particles as a vertical axis, as shown in FIG. 1.

Specifically, the content ratio (volume ratio) of the fine powder having a particle diameter of 150 µm or less, 100 µm or less, or 50 µm or less can be determined from the volume-based particle size distribution based on the following formula.

$$X_l = \frac{\sum_{k=1}^{b} X_k * D_k^3}{\sum_{i=1}^{n} X_i * D_i^3} \times 100 \qquad \text{[Formula 4]}$$

In the above formula, $X_i$ is a content ratio (volume ratio (%)) of a fine powder having a particle diameter of 150 µm or less, 100 µm or less, or 50 µm or less, $D_k$ is any particle diameter µm) having a particle diameter of 150 µm or less, 100 µm or less, or 50 µm or less, and $X_k$ is a content ratio (volume ratio) of particles at the particle diameter $D_k$. $X_i$ and $D_i$ are the same as in the above formula (1). The content ratio (volume ratio) of the particles at the particle diameter $D_k$ means the ratio of the volume of the granules having the particle diameter $D_k$ to the volume of the entire granules, and means $V_k/V$ where V is the volume of the entire granules, and $V_k$ is the volume of the granules having the particle diameter $D_k$.

The amino acid-containing granules according to the present embodiment preferably have a specific surface area of 0.30 m²/g or more. When the specific surface area is 0.30 m²/g or more, the contact area with water is large, so that the amino acid-containing granules can melt easily in the mouth and can be sufficiently dissolved in water.

The specific surface area of the amino acid-containing granules according to the present embodiment is preferably 0.35 m²/g or more, more preferably 0.40 m²/g or more, and still more preferably 0.42 m²/g or more.

The specific surface area of the amino acid-containing granules is, for example, 1.0 m²/g or less, 0.8 m²/g or less, or 0.6 m²/g or less.

The specific surface area of the amino acid-containing granules according to the present embodiment is a specific surface area measured by a BET method. As a device, for example, a BET specific surface area meter (trade name: Macsorb, manufactured by Mountech Co., Ltd.) can be used.

The amino acid-containing granules according to the present embodiment preferably have a bulk specific gravity of 0.30 g/mL or more. When the bulk specific gravity is 0.30 g/mL or more, the amino acid-containing granules are easy to be swallowed because the amino acid-containing granules do not become bulky in an oral cavity when taken directly.

The bulk specific gravity of the amino acid-containing granules according to the present embodiment is preferably 0.35 g/mL or more, more preferably 0.40 g/mL or more, and still more preferably 0.42 g/mL or more.

The bulk specific gravity of the amino acid-containing granules is, for example, 0.70 g/mL or less, 0.65 g/mL or less, or 0.55 g/mL or less.

The bulk specific gravity refers to a weight per volume of granules, that is, an apparent specific gravity, and is determined by filling a container having a constant internal volume with granules, measuring a weight thereof, and then calculating a value obtained by dividing a difference between the obtained weight and a weight of the container by an internal volume of the container.

In the measurement of the bulk specific gravity of the amino acid-containing granules according to the present embodiment, an instrument for measuring bulk specific gravity of powder or an instrument for measuring a powder and powder body characteristic in accordance with a standard such as JIS K-6721 is used, and for example, an instrument for measuring a powder and powder body characteristic, manufactured by Tsutsui Scientific Instruments Co., Ltd., is used.

The amino acid-containing granules according to the present embodiment preferably have a powdering ratio of 5% or more. The powdering ratio is an index of breakability (hardness) of the granules, and when the powdering ratio is 5% or more, the granules are easily broken in the oral cavity, and the easiness of swallowing the granules is improved.

The powdering ratio of the amino acid-containing granules according to the present embodiment is preferably 10% or more, more preferably 12% or more, still more preferably 15% or more, yet still more preferably 20% or more, still further more preferably 25% or more, yet still further more preferably 30% or more, and even more preferably 35% or more.

The powdering ratio of the amino acid-containing granules is, for example, 50% or less, 45% or less, or 40% or less.

The powdering ratio of the amino acid-containing granules according to the present embodiment represents the easiness of powdering of the granules, and means a value obtained by the following procedure (1) to (5).

(1) A sample is sieved with a sieve having a size of mesh opening of 250 μm for 1 minute at a frequency of 100 times/sec and an amplitude of 2 mm, and granules having a particle diameter of 250 μm or less are removed.

(2) 10 g of granules remaining on the sieve is weighed out and taken as a "weight of original sample granules".

(3) 10 g of the granules weighed in (2) above is put into the sieve having a size of mesh opening of 250 μm with five tapping balls (diameter: 20 mm), and wear and impact are applied to the granules at a frequency of 100 times/sec and an amplitude of 2 mm for 15 minutes.

(4) A weight of granules dropped under the sieve is measured, and is defined as a "weight of newly generated fine powder".

(5) The powdering ratio is determined by the following formula.

$$\text{Powdering ratio (\%)} = (\text{weight of newly generated fine powder}/\text{weight of original sample granules}) \times 100$$

A circular sieve having a diameter of 100 mm can be used as the sieve. For the measurement of the powdering ratio, for example, an electromagnetic vibration sieving machine M-100 manufactured by Tsutsui Scientific Instruments Co., Ltd., can be used.

The amino acid-containing granules according to the present embodiment can contain components other than the amino acid as long as the effects of the present invention are not impaired. Examples of components other than the amino acid include a sweetener, an excipient, a binder, various nutrients, an acidulant, a fragrance, a stabilizer, a preservative, an antiseptic, a fungicide, and an antioxidant. As these components, those commonly used in the production of foods, pharmaceuticals, and the like can be suitably used.

Note that, as described above, the amino acid-containing granules according to the present embodiment can melt easily in the mouth and have sufficiently high water solubility due to adjusting the average particle diameter and the homogeneity U to specific ranges. This is because the granules having a large particle diameter have a small specific surface area and a small contact area with water or the like, and thus it takes time to dissolve the granules. This is because the granules having a small particle diameter are easy to scatter, leads to choking and sticking to a throat, and thus the granules are hard to be swallowed. This is also because the granules having a small particle diameter have a large specific surface area, form a lump in which only a surface of the granules is wet, and this results in a decrease in solubility. In this way, specifying the ranges of the average particle diameter and the homogeneity U is important for improving the solubility and the easiness of swallowing of the amino acid-containing granules. Therefore, even when components other than the amino acid are contained, the amino acid-containing granules that can melt easily in the mouth and have sufficiently high water solubility can be obtained by adjusting the average particle diameter and the homogeneity U to specific ranges.

In the present embodiment, as the sweetener, any sweetener commonly used in foods and pharmaceuticals can be used, and the sweetener may be either a natural sweetener or a synthetic sweetener. The sweetener is not limited, but examples of the sweetener include glucose, fructose, maltose, sucrose, oligosaccharide, sugar, granulated sugar, maple syrup, honey, molasses, trehalose, palatinose, maltitol, xylitol, sorbitol, glycerin, aspartame, advantame, neotame, sucralose, acesulfame potassium, and saccharin. These may be used alone or in combination.

When the amino acid-containing granules contain a sweetener, the content of the sweetener is preferably 0 to 15 mass %, more preferably 0 to 12 mass %, and still more preferably 0 to 10 mass %, with respect to the amino acid-containing granules, from the viewpoint of improvement in flavor and palatability, and from the viewpoint of masking bitterness peculiar to amino acids.

In the present embodiment, as the excipient, any excipient commonly used in foods and pharmaceuticals can be used. The excipient is not limited, but examples of the excipient include saccharides, sugar alcohol, starches, celluloses, and an inorganic excipient. Examples of the saccharides include lactose, sucrose, fructooligosaccharide, glucose, palatinose, reduced palatinose, maltose, reduced maltose, powder sugar, powder syrup, fructose, isomerized lactose, and honey sugar. Examples of the sugar alcohol include D-mannitol, erythritol, xylitol, maititol, and sorbitol. Examples of the starches include corn starch, potato starch, coniere starch, partial alpharized starch, and alpharized starch. Examples of the celluloses include crystalline cellulose, powder cellulose, hydroxypropyl cellulose, carmellose, carmellose calcium, and croscarmellose sodium. These may be used alone or in combination.

When the amino acid-containing granules contain an excipient, the content of the excipient is preferably 0 to 50 mass %, more preferably 0 to 40 mass %, and still more preferably 0 to 35 mass %, with respect to the amino acid-containing granules, from the viewpoint of improvement in production suitability.

In the present embodiment, the acidulant is not limited, but examples of the acidulant include acetic acid, citric acid, anhydrous citric acid, adipic acid, succinic acid, lactic acid, malic acid, phosphoric acid, gluconic acid, tartaric acid, and salts thereof. In the present embodiment, the granules contains the acidulant, bitterness caused by the type of amino acid can be suppressed (masked). These may be used alone or in combination.

When the amino acid-containing granules contain an acidulant, the content of the acidulant is preferably 0 to 30 mass %, more preferably 0 to 25 mass %, and still more preferably 0 to 20 mass %, with respect to the amino acid-containing granules, from the viewpoint of nutritional design and improvement in flavor and palatability.

Examples of the carbohydrate include sucrose, glucose, maltose, fructose, lactose, erythritol, trehalose, sorbitol, maltitol, xylitol, oligosaccharide, and soluble starch. When the amino acid-containing granules contain carbohydrate, the content of the carbohydrate is preferably 0.3 mass % to 50.0 mass %, more preferably 0.5 mass % to 40.0 mass %, and still more preferably 0.7 mass % to 35.0 mass %, with respect to the granules, from the viewpoint of nutritional design.

Examples of the fragrance include vanilla fragrance, milk fragrance, fruit fragrance, and drink fragrance. When the amino acid-containing granules contain a fragrance, the content of the fragrance is preferably 0.5 mass % to 6.0 mass %, more preferably 1.0 mass % to 5.0 mass %, and still more preferably 1.2 mass % to 4.0 mass %, with respect to the granules, from the viewpoint of improvement in flavor and palatability.

Examples of the binder include thickening polysaccharides such as pullulan, gum arabic, guar gum, xanthan gum, locust bean gum, and dextrin. When the amino acid-containing granules contain a binder, the content of the binder is preferably 0.4 mass % to 3.0 mass %, more preferably 0.6 mass % to 2.0 mass %, and still more preferably 0.8 mass % to 1.5 mass %, with respect to the granules, from the viewpoint of allowing the particles to bind to each other and from the viewpoint of improvement in solubility.

In particular, the amino acid-containing granules of the present embodiment preferably contain carbohydrates, an acidulant, a fragrance, a sweetener, and thickening polysaccharides.

The amino acid-containing granules according to the present embodiment can be in a form of a health food, a specific health food, a nutritional functional food, a supplement, a food with functional claims, a medicine, and the like, for replenishing an amino acid. The amino acid-containing granules according to the present embodiment contain the amino acid at a high concentration, and thus, these products allows for reducing the intake of the product at one time. In addition, the amino acid-containing granules according to the present embodiment can melt easily in the mouth and have good water solubility, and thus, a consumer can easily take the amino acid-containing granules.

The amino acid-containing granules according to the present embodiment are granulated so as to satisfy the average particle diameter and the homogeneity U in specific ranges. The specific surface area, the bulk specific gravity, the powdering ratio, the content ratio of the fine powder, and the like are adjusted as necessary. Those skilled in the art can set the average particle diameter, the homogeneity U, and the like in the specific ranges by appropriately selecting various conditions using a common known mixing method or granulation method described below.

The amino acid-containing granules according to the present embodiment can be produced through a step of mixing an amino acid powder and other components, and a step of granulating the obtained mixture. Such a production method may include a step of classifying the granules obtained in the granulation step by sieving. This will be described in detail below.

In order to obtain the amino acid-containing granules according to the present embodiment, first, the whey protein powder is mixed with other optional components as necessary. The mixing method is not limited, and can be performed by a method typically used in the related art. For example, a horizontal cylinder type mixer, a V type mixer, a double cone type mixer, a swing rotation type mixer, a single axis ribbon type mixer, a double axis paddle type mixer, a rotating operation type mixer, a conical screw type mixer can be used for the mixing. In addition, granulation may be performed simultaneously with mixing of various components in the granulation process described below.

Subsequently, the mixture obtained as described above can be granulated by a general granulation method. The granulation method is not limited. Both of dry granulation and wet granulation can be used.

Examples of the dry granulation include a slag method and a roller compactor method. Examples of the wet granulation include stirring and mixing granulation, spray drying granulation, fluidized bed granulation, tumbling granulation, tumbling fluidized bed granulation, and extrusion granulation.

The stirring and mixing granulation is a granulation method in which water and a binder are added to stirred particles, followed by shearing, tumbling, and compacting actions by rotation of blades having various shapes to proceed with crosslinking formation between the particles, to repeat generation, bonding (association) and crushing (dissociation) of fine particles and to cause growth of the particles to form granulated particles.

The spray drying granulation is a granulation method in which a liquid is dispersed and dried in a high-temperature air stream.

The fluidized bed granulation is a granulation method in which powder is coagulated and granulated with water and a binder sprayed while a powder layer is kept in a fluidized state on a fluidized bed such as a normal fluidized bed, a circulating fluidized bed, a forced circulating fluidized bed, or a spouted bed.

The tumbling granulation is a granulation method in which raw material powders of particles are tumbled in various containers by the action of stirring blades with water and a binder sprayed to form fine particles by crosslinking formation between particles, and the growth of the particles is promoted by applying tumbling and rotating motions to the particles. The tumbling granulation is performed using a dish-type (ban-type) granulator, a drum-type granulator, a vibration-type granulator, or the like.

The tumbling fluidized bed granulation is a mechanism having the characteristics of both the stirring granulation and the fluidized bed granulation and is a granulation method in which granulated particles are formed by tumbling, flowing, and stirring particles with water and a binder sprayed to advance the crosslinking formation between the particles.

The extrusion granulation refers to granulating powder by mixing and kneading it with water and a binder added, and extruding a plasticized powder from a screen or die having a large number of holes with a screw, a roller, or the like. The extrusion granulation is performed using a front extrusion granulator, a disc pelleter granulator, a ring die granulator, a basket granulator, an oscillating granulator, a cylinder granulator, or the like.

In the wet granulation, for example, when a fluidized bed granulation method is adopted, a common known fluidized bed granulation device can be used. In this device, a fluid such as air is blown up from a lower portion of the device, solid particles (raw material powders) are allowed to float (flowing), and a spray liquid such as water or a binder is sprayed on the solid particles to perform granulation and drying. A commercially available fluidized bed granulator can be used as the fluidized bed granulator. Examples of the operation conditions to be adjusted at this time include a type of the spray liquid, a spray liquid amount, a spray flow rate, a blowing air amount, a blowing air temperature, an exhaust air temperature, and a damper opening degree.

As the binder, those typically used in the related art can be used. Examples of the binder include cellulose derivatives such as methyl cellulose, hydroxypropyl cellulose, hypromellose, and hypromellose phthalate; starches such as corn starch, wheat starch and pullulan; synthetic polymers such as polyvinyl pyrrolidone and acrylic acid polymers; and natural polymers such as gum arabic and gelatin. The amount of the binder to be used can be limited to an extent that normal granulation is possible.

For example, when granulation is performed by fluidized bed granulation, the specific average particle diameter, homogeneity U, specific surface area, bulk specific gravity, content ratio of a fine powder, and the like in the present embodiment can be specifically realized by appropriately adjusting a supply air flow rate, a supply air temperature, a binder flow rate, a binder liquid droplet diameter, and the like.

Hereinafter, specific granulation conditions in the case of using a fluidized bed granulator will be exemplified, but the granulation conditions are not limited.

Size at time of introduction of amino acid: 5 μm to 100 μm
Amount at time of introduction of amino acid: 200 g to 1000 g
Supply air temperature (granulation): 50° C. to 150° C.
Supply air temperature (drying): 50° C. to 150° C.
Supply air flow rate (granulation): 0.1 m³/min to 1.0 m³/min
Supply air flow rate (drying): 0.1 m³/min to 1.0 m³/min
Binder flow rate: 5 g/min to 50 g/min
Amount of binder to be added: 30 g to 500 g
Spray air flow rate: 10 L/min to 60 L/min
Granulation time: 20 minutes to 40 minutes If necessary, the granules obtained above may be further classified by sieving.

The thus-obtained amino acid-containing granules according to the present embodiment can melt easily in the mouth and is easily swallowed.

In addition, when the amino acid-containing granules are dissolved in water, the amount of the undissolved granules is small, and thus, the mixture is easily swallowed, since the water solubility is sufficiently high. For example, a residual weight (dry weight) of the granules is 1 g or less, preferably 0.8 g or less, more preferably 0.7 g or less, still more preferably 0.5 g or less, and yet still more preferably 0.4 g or less, when 7 g of the granules is added to a container containing 100 ml of water, the mixture is stirred and then sieved with a sieve having a size of mesh opening of 150 μm, and granules remaining on the sieve are dried at 98° C. for 4 hours. When the residual weight of the granules is within the above range, the amount of undissolved granules is small, and thus the mixture is easily swallowed.

EXAMPLE

Hereinafter, the present invention will be further described with reference to Examples and Comparative Examples, but the present invention is not limited to the following Examples.
[Measurement Method]
A measurement method used in the present example will be described below.

[Average Particle Diameter, Homogeneity U, Content Ratio of Fine Powder]
A volume-based particle size distribution was obtained by using Mastersizer 3000 (manufactured by Malvern Co., Ltd.) and the included soft Mastersizer 3000, as a laser diffraction and scattering particle size distribution measuring device. The data was plotted with a particle diameter as a horizontal axis and with a content ratio of particles as a vertical axis. For the measurement conditions, a hopper gap was set to 2 mm, a feeder strength was set to 20% to 40%, and an air pressure of powder conveyance was set to 0.2 bar to 0.5 bar.

From the obtained volume-based particle size distribution, an average particle diameter (median diameter), and a fine powder having a particle diameter of 150 μm or less, 100 μm or less, or 50 μm or less were determined. A homogeneity U was determined from the following formula (1) based on the obtained volume-based particle size distribution.

[Formula 5]

$$U = \frac{\sum X_i |D_i - D_p|}{D_p} \tag{1}$$

In the formula (1), $D_p$, is an average particle diameter (μm), $X_i$ is a content ratio of particles at each particle diameter in the volume-based particle size distribution, and $D_i$ is a particle diameter (μm) of each particle.
[Specific Surface Area]
A specific surface area of the granules was determined using a BET specific surface area meter (trade name: Macsorb, manufactured by Mountech Co., Ltd.).
[Bulk Specific Gravity]
A hulk specific gravity of the granules was measured in accordance with a standard of JIS K-6271 using a powder and powder body measuring device manufactured by Tsutsui Scientific Instruments Co., Ltd.
[Powdering Ratio]
A powdering ratio was measured by using an electromagnetic vibration sieving machine M-100 manufactured by Tsutsui Scientific Instruments Co., Ltd., according to the following procedure (1) to (5). A circular sieve having a diameter of 100 mm was used as the sieve.

(1) A sample was sieved with a sieve having a size of mesh opening of 250 μm for 1 minute at a frequency of 100 times/sec and an amplitude of 2 mm, and granules having a particle diameter of 250 μm or less were removed.

(2) 10 g of granules remaining on the sieve was weighed out and taken as a "weight of original sample granules".

(3) 10 g of the granules weighed in (2) above was put into the sieve having a size of mesh opening of 250 μm with five tapping balls (diameter: 20 mm), and wear and impact were applied to the granules at a frequency of 100 times/sec and an amplitude of 2 mm for 15 minutes.

(4) A weight of the granules dropped under the sieve was measured, and was defined as a "weight of newly generated fine powder".

(5) The powdering ratio was determined by the following formula.

$$\text{Powdering ratio (\%)} = (\text{weight of newly generated fine powder/weight of original sample granules}) \times 100$$

Production Example 1

The following components were mixed to prepare an amino acid-containing composition 1 before granulation.
Amino acid (containing L-arginine, L-phenylalanine, and L-alanine)
Acid Want (citric acid (anhydride))
Carbohydrate (erythritol)
Fragrance (lemon fragrance, grapefruit fragrance)
Sweetener The prepared composition 1 was introduced into a fluidized bed granulator together with an aqueous solution of thickening polysaccharides (pullulan, gum arabic, dextrin, and xanthan gum) as a liquid component (binder) to obtain a granule having a composition shown in Table 1. Four types of granules A to D shown in Table 2 were obtained by changing an amount of the binder to be added, a spray air flow rate, and the like.

A particle diameter of the composition 1 before granulation was set to 5 μm to 100 μm, and a granulation time was set to 20 minutes to 40 minutes.

Subsequently, the water solubility of the obtained granules A to D was evaluated by the following method.

7 g of the granules was added to a 300 ml beaker containing 100 ml of water at 25° C., the mixture was stirred for 10 seconds at a peripheral speed of 0.5 m/sec by a stirrer, the granules after stirring were sieved with a sieve having a size of mesh opening of 150 μm, granules remaining on the sieve were dried at 98° C. for 4 hours by a thermostat, and a residual weight (dry weight) was measured to evaluate the water solubility. The results are shown in Table 2 below.

TABLE 1

| Raw materials | Mixing ratio (mass %) |
|---|---|
| Amino acid | 52.5 |
| Acidulant | 10 |
| Carbohydrate | 32.4 |
| Fragrance | 1.6 |
| Sweetener | 2.5 |
| Thickening polysaccharide | 1.0 |
| Total | 100 |

From the results in Table 2, it was found that a residue weight was 1 g or less in the granules A to D having an average particle diameter of 150 μm to 500 μm and a homogeneity U of 0.70 or less, and the granules A to D exhibited excellent water solubility.

Production Example 2

The following components were mixed to prepare an amino acid-containing composition 2 before granulation.
Amino acid (containing L-arginine, L-valine, and L-serine)
Acidulant (citric acid (anhydride))
Carbohydrate (erythritol)
Fragrance (lemon fragrance, grapefruit fragrance)
Sweetener The prepared composition 2 was introduced into a fluidized bed granulator together with an aqueous solution of thickening polysaccharides as a liquid component (binder) to obtain a granule E having a composition shown in Table 3 and having physical properties shown in Table 4. A particle diameter of the composition 1 before granulation was set to 5 μm to 100 μm, and a granulation time was set to 20 minutes to 40 minutes.

In addition, the water solubility of the obtained granule E was evaluated in the same manner as in Production Example 1. The results are shown in Table 4 below.

TABLE 3

| Raw materials | Mixing ratio (mass %) |
|---|---|
| Amino acid | 76 |
| Acidulant | 17.5 |
| Carbohydrate | 0.6 |
| Fragrance | 3.0 |
| Sweetener | 1.7 |
| Thickening polysaccharide | 1.2 |
| Total | 100 |

TABLE 2

| | | | Production Example 1 | | | | | | |
|---|---|---|---|---|---|---|---|---|---|
| | Average particle | | Fine powder | | | Specific surface | Bulk specific | | |
| Granule | diameter (μm) | Homogeneity U | 50 μm or less (%) | 100 μm or less (%) | 150 μm or less (%) | area (m²/g) | gravity (g/mL) | Powdering ratio (%) | Residual weight (g) |
| A | 235 | 0.507 | 5.15 | 15.33 | 29.43 | 0.438 | 0.478 | 17.2 | 0.20 |
| B | 221 | 0.649 | 11.81 | 22.69 | 35.84 | — | 0.497 | 28.0 | 0.25 |
| C | 484 | 0.439 | 2.34 | 4.03 | 6.24 | — | 0.393 | 12.3 | 0.29 |
| D | 434 | 0.420 | 1.21 | 3.16 | 6.08 | — | 0.366 | 12.2 | 0.36 |

TABLE 4

| | | | | Fine powder | | Specific surface | Bulk specific | | |
|---|---|---|---|---|---|---|---|---|---|
| | Average particle | | | | | | | | |
| Granule | diameter (μm) | Homogeneity U | 50 μm or less (%) | 100 μm or less (%) | 150 μm or less (%) | area (m²/g) | gravity (g/mL) | Powdering ratio (%) | Residual weight (g) |
| E | 219 | 0.480 | 6.15 | 15.04 | 31.29 | 0.565 | 0.440 | 36.7 | 0.71 |

*Production Example 2*

From the results in Table 4, it was found that a residue weight was 1 g or less in the granule E having an average particle diameter of 150 μm to 500 μm and a homogeneity U of 0.70 or less, and the granule E exhibited excellent water solubility.

[Commercially Available Product 1]

As a commercially available product 1 of the amino acid-containing granules, an aminovital pro (manufactured by Ajinomoto Co., Inc.) was used. The commercially available product 1 contains about 80 mass % of amino acid (amino acid content is 3600 mg in 4.5 g of the product). Measurement results of the average particle diameter, the homogeneity U, the content ratio of the fine powder, and the powdering ratio of the commercially available product 1 are shown in Table 5.

In addition, the results of evaluating the water solubility of the commercially available product 1 in the same manner as in Production Example 1 are shown in the following Table 5.

TABLE 5

| | Average particle | | Fine powder | | | | |
|---|---|---|---|---|---|---|---|
| Commercially available product | diameter (μm) | Homogeneity U | 50 μm or less (%) | 100 μm or less (%) | 150 μm or less (%) | Powdering ratio (%) | Residual weight (g) |
| 1 | 1270 | 0.421 | 0.75 | 1.98 | 3.27 | 2.8 | 1.51 |

From the results shown in Table 5, it was found that a residue weight exceeded 1 g in the commercially available product 1 having an average particle diameter outside the range of 150 μm to 500 μm, and the water solubility was inferior.

[Commercially Available Product 2]

As a commercially available product 2 of the amino acid-containing granules, Aminopic FOR ACTIVE (manufactured by Ajinomoto Co., Inc.) was used. The commercially available product 2 contains about 73 mass % of amino acid (amino acid content is 2200 mg in 3.0 g of the product). Measurement results of the average particle diameter, the homogeneity U, the content ratio of the fine powder, the specific surface area, the bulk specific gravity, and the powdering ratio of the commercially available product 2 are shown in Table 6.

In addition, the results of evaluating the water solubility of the commercially available product 2 in the same manner as in Production Example 1 are shown in the following Table 6.

TABLE 6

| | Average particle | | Fine powder | | | Specific surface | Bulk specific | | |
|---|---|---|---|---|---|---|---|---|---|
| Commercially available product | diameter (μm) | Homogeneity U | 50 μm or less (%) | 100 μm or less (%) | 150 μm or less (%) | area (m²/g) | gravity (g/mL) | Powdering ratio (%) | Residual weight (g) |
| 2 | 865 | 0.757 | 1.77 | 7.49 | 14.45 | 0.287 | 0.538 | 4.3 | 1.68 |

From the results shown in Table 6, it was found that a residue weight exceeded 1 g in the commercially available product 2 having an average particle diameter outside the range of 150 μm to 500 μm and a homogeneity U exceeding 0.70, and the water solubility was inferior.

Sensory Evaluation Test

For 100 people of male and female amino acid-containing granule users (people who take amino acid-containing granule products al least twice a month) between the ages of 20 and 59, 3.0 g of the granules A produced as described above and the commercially available products 2 were taken directly orally, and a home use test was conducted for it evaluation items of meltability in the mouth and swallowability (easiness of swallowing).

The "meltability in the mouth" means that when granules are put into a mouth, the granules melt well and quickly melt, and the "swallowability (easiness of swallowing)" means smoothness of the product through a throat during swallowing.

The sensory evaluation (meltability in the mouth and swallowability (easiness of swallowing)) was performed according to the following evaluation criteria.

Granule A is very good

Granule A is rather good

I cannot say either way

Commercially available product 2 is rather good

Commercially available product 2 is very good

The results are shown in FIG. 2. The granule A was found to be superior to the commercially available product 2 in terms of meltability in the mouth and swallowability (easiness of swallowing).

Although various embodiments have been described above with reference to the drawings, it is needless to say that the present invention is not limited to such examples. It is apparent to those skilled in the art that various changes and modifications can be conceived within the scope of the claims, and it is also understood that such variations and modifications belong to the technical scope of the present invention. In addition, constituent elements in the embodiments described above may be combined freely within a range not departing from the spirit of the present invention.

The present application is based on Japanese Patent Application No. 2019-172259 filed on Sep. 20, 2019, the contents of which are incorporated herein by reference.

The invention claimed is:

1. Amino acid-containing granules comprising an amino acid as a main component, wherein the amino acid-containing granules have an average particle diameter of 150 μm to 500 μm, and a homogeneity U of 0.70 or less, and wherein the average particle diameter and the homogeneity U are determined by the following measurement method:

a) a volume-based particle size distribution in which data is plotted with a particle diameter as a horizontal axis and a content ratio (volume ratio) of particles as a vertical axis is obtained for the granules by a laser diffraction and scattering measurement method, b) the average particle diameter is determined from the volume-based particle size distribution, and c) the homogeneity U is determined by the following formula (1), $$U = \frac{\sum X_i |D_i - D_p|}{D_p} \qquad (1)$$

where, in the formula (1), $D_p$ is an average particle diameter (μm), $X_i$ is content ratio (volume ratio) of particles at each particle diameter in the volume-based particle size distribution, and $D_i$ is a particle diameter (μm) of each particle, wherein the amino acid includes L-arginine, wherein the amino acid-containing granules comprise thickening polysaccharide, and wherein the amino acid-containing granules have a bulk specific gravity of between 0.3 g/mL and 0.497 g/mL.

2. The amino acid-containing granules according to claim 1, wherein the amino acid-containing granules have a specific surface area of 0.30 m²/g or more.

3. The amino acid-containing granules according to claim 1, wherein the amino acid-containing granules have the content ratio (volume ratio) of a fine powder having a particle diameter of 100 μm or less of 25% or less.

4. The amino acid-containing granules according to claim 1, wherein the amino acid-containing granules have an amino acid content of 50 mass % or more.

5. The amino acid-containing granules according to claim 1, wherein the amino acid-containing granules have a powdering ratio of 5% or more, and wherein the powdering ratio means a value obtained by the following procedure (1) to (5), (1) the amino acid-containing granules are sieved with a sieve having a size of mesh opening of 250 μm for 1 minute at a frequency of 100 times/sec and an amplitude of 2 mm, and granules having a particle diameter of 250 μm or less are removed, (2) 10 g of granules remaining on the sieve is weighed out and taken as a "weight of original sample granules", (3) 10 g of the granules weighed in (2) above is put into the sieve having a size of mesh opening of 250 μm with five tapping balls (diameter: 20 mm), and wear and impact are applied to the granules at a frequency of 100 times/sec and an amplitude of 2 mm for 15 minutes, (4) a weight of the granules dropped under the sieve is measured, and is defined as a "weight of newly generated fine powder", and (5) the powdering ratio is determined by the following formula, Powdering ratio (%)=(weight of newly generated fine powder/weight of original sample granules)×100.

6. The amino acid-containing granules according to claim 1, wherein a residual weight of the granules is 1 g or less, when 7 g of the granules is added to 100 ml of water and stirred to form a mixture, then the mixture is sieved with a sieve having a size of mesh opening of 150 μm, and granules remaining on the sieve are dried at 98° C. for 4 hours.

7. The amino acid-containing granules according to claim 2, wherein the amino acid-containing granules have the content ratio (volume ratio) of a fine powder having a particle diameter of 100 μm or less of 25% or less.

8. The amino acid-containing granules according to claim 2, wherein the amino acid-containing granules have an amino acid content of 50 mass % or more.

9. The amino acid-containing granules according to claim 3, wherein the amino acid-containing granules have an amino acid content of 50 mass % or more.

10. The amino acid-containing granules according to claim 7, wherein the amino acid-containing granules have an amino acid content of 50 mass % or more.

11. The amino acid-containing granules according to claim 2, wherein the amino acid-containing granules have a powdering ratio of 5% or more, and wherein the powdering ratio means a value obtained by the following procedure (1) to (5), (1) the amino acid-containing granules are sieved with a sieve having a size of mesh opening of 250 μm for 1 minute at a frequency of 100 times/sec and an amplitude of 2 mm, and granules having a particle diameter of 250 μm or less are removed, (2) 10 g of granules remaining on the sieve is weighed out and taken as a "weight of original sample granules", (3) 10 g of the granules weighed in (2) above is put into the sieve having a size of mesh opening of 250 μm with five tapping balls (diameter: 20 mm), and wear and impact are applied to the granules at a frequency of 100 times/sec and an amplitude of 2 mm for 15 minutes, (4) a weight of the granules dropped under the sieve is measured, and is defined as a "weight of newly generated fine powder", and (5) the powdering ratio is determined by the following formula, Powdering ratio (%)=(weight of newly generated fine powder/weight of original sample granules)×100.

12. The amino acid-containing granules according to claim 3, wherein the amino acid-containing granules have a powdering ratio of 5% or more, and wherein the powdering ratio means a value obtained by the following procedure (1) to (5), (1) the amino acid-containing granules are sieved with a sieve having a size of mesh opening of 250 μm for 1 minute at a frequency of 100 times/sec and an amplitude of 2 mm, and granules having a particle diameter of 250 μm or less are removed, (2) 10 g of granules remaining on the sieve is weighed out and taken as a "weight of original sample granules", (3) 10 g of the granules weighed in (2) above is put into the sieve having a size of mesh opening of 250 μm with five tapping balls (diameter: 20 mm), and wear and impact are applied to the granules at a frequency of 100 times/sec and an amplitude of 2 mm for 15 minutes, (4) a weight of the granules dropped under the sieve is measured, and is defined as a "weight of newly generated fine powder", and (5) the powdering ratio is determined by the following formula, Powdering ratio (%)=(weight of newly generated fine powder/weight of original sample granules)×100.

13. The amino acid-containing granules according to claim 1, wherein the thickening polysaccharide is selected from the group consisting of pullulan, gum arabic, dextrin, and xanthan gum.

* * * * *